(12) United States Patent
Stenbeck et al.

(10) Patent No.: US 10,060,429 B2
(45) Date of Patent: Aug. 28, 2018

(54) CONDUCTIVITY SENSOR, AND A PUMP COMPRISING SUCH SENSOR

(71) Applicant: Tetra Laval Holdings & Finance S.A., Pully (SE)

(72) Inventors: Johan Stenbeck, Malmö (SE); Fredrik Johansson, Lund (SE)

(73) Assignee: TETRA LAVAL HOLDINGS & FINANCE S.A., Pully (CH)

( * ) Notice: Subject to any disclaimer, the term of this patent is extended or adjusted under 35 U.S.C. 154(b) by 138 days.

(21) Appl. No.: 15/106,654

(22) PCT Filed: Dec. 19, 2014

(86) PCT No.: PCT/EP2014/078787
§ 371 (c)(1),
(2) Date: Jun. 20, 2016

(87) PCT Pub. No.: WO2015/091976
PCT Pub. Date: Jun. 25, 2015

(65) Prior Publication Data
US 2017/0016440 A1    Jan. 19, 2017

(30) Foreign Application Priority Data
Dec. 20, 2013   (SE) ...................................... 1351545

(51) Int. Cl.
*F04B 51/00* (2006.01)
*F04B 43/00* (2006.01)
(Continued)

(52) U.S. Cl.
CPC ............ *F04B 51/00* (2013.01); *F04B 43/009* (2013.01); *F04B 43/0054* (2013.01);
(Continued)

(58) Field of Classification Search
None
See application file for complete search history.

(56) References Cited

U.S. PATENT DOCUMENTS 3,774,104 A * 11/1973 Andersen ............... G01N 27/06
324/429
3,953,154 A     4/1976 Wanner
(Continued)

FOREIGN PATENT DOCUMENTS

DE    26 24 129 A1    3/1977
DE    29 43 509 B1    1/1981
(Continued)

OTHER PUBLICATIONS

International Search Report (PCT/ISA/210) dated Mar. 26, 2015, by the Japanese Patent Office as the International Searching Authority for International Application No. PCT/EP2014/078787.
(Continued)

*Primary Examiner* — Paul West
*Assistant Examiner* — Mark A Shabman
(74) *Attorney, Agent, or Firm* — Renner Otto Boisselle & Sklar, LLP

(57) ABSTRACT

A conductivity sensor is provided. The sensor comprises at least one electrode being embedded in a cylindrical non-conductive body such that one end of each one of the at least one electrode is exposed to a sample volume, wherein the sensor further comprises a support body to which the cylindrical body is engagable with, which support body comprises means for attaching said support body to a frame structure in a fluid tight manner.

13 Claims, 4 Drawing Sheets

(51) Int. Cl.
*F04B 43/08* (2006.01)
*G01N 27/07* (2006.01)
*G01N 27/10* (2006.01)
*G01N 33/04* (2006.01)

(52) U.S. Cl.
CPC ............. *F04B 43/08* (2013.01); *G01N 27/07* (2013.01); *G01N 27/10* (2013.01); *G01N 33/04* (2013.01)

(56) References Cited

U.S. PATENT DOCUMENTS

| | | | | |
|---|---|---|---|---|
| 4,283,261 | A * | 8/1981 | Maurer | G01N 27/4071 204/408 |
| 4,331,923 | A * | 5/1982 | Akers, Jr. | G01R 27/22 324/442 |
| 4,430,048 | A * | 2/1984 | Fritsch | F04B 43/067 417/383 |
| 4,489,596 | A * | 12/1984 | Linder | H01T 13/18 313/137 |
| 4,832,581 | A * | 5/1989 | Muller | F04B 43/067 417/383 |
| 4,971,523 | A * | 11/1990 | Wacker | F04B 43/009 340/605 |
| 6,174,144 | B1 * | 1/2001 | van Hamme | F04B 43/0009 417/339 |
| 6,327,891 | B1 * | 12/2001 | Noda | G01N 27/407 204/424 |
| 6,634,210 | B1 * | 10/2003 | Bosch | G01N 15/0656 204/426 |
| 8,161,796 | B2 * | 4/2012 | Nair | G01N 15/0656 73/23.33 |
| 2006/0162422 | A1 * | 7/2006 | Geier | G01N 27/407 73/23.31 |
| 2011/0252865 | A1 * | 10/2011 | Tokuda | G01N 15/0656 73/23.31 |
| 2012/0011998 | A1 * | 1/2012 | Johansson | F04B 43/067 92/47 |

FOREIGN PATENT DOCUMENTS

| | | |
|---|---|---|
| EP | 0 359 556 A1 | 3/1990 |
| EP | 0 515 914 A1 | 12/1992 |
| JP | H11 304311 A | 11/1999 |

OTHER PUBLICATIONS

Written Opinion (PCT/ISA/237) dated Mar. 26, 2015, by the Japanese Patent Office as the International Searching Authority for International Application No. PCT/EP2014/078787.

Swedish Search Report dated Jun. 30, 2014, issued by the Swedish Patent Office in the corresponding Swedish Patent Application No. 1351545-7. (7 pages).

* cited by examiner

CONDUCTIVITY SENSOR, AND A PUMP COMPRISING SUCH SENSOR

TECHNICAL FIELD

The present invention relates to a conductivity sensor. More particularly, the present invention relates to a conductivity sensor for use in a diaphragm pump, as well as such diaphragm pump.

BACKGROUND

Conductivity sensors are normally provided in order to detect the actual conductivity of fluids, such as gases or liquid solutions. The general principle is based on the fact that the electrical conductivity is a very specific property of fluids. A change in composition or temperature will provide a change in conductivity. Hence, by measuring the conductivity variations within a system may easily be detected.

Different methods for measuring conductivity have been proposed, in which one includes the provision of four concentrically arranged electrodes. An alternating current is supplied to the outer pair of electrodes, whereby the potential of the inner pair of electrodes is probed as a measure of the actual conductivity of the media surrounding the electrodes.

It has been suggested to use conductivity measurements for determining the presence of leaks in a double membrane diaphragm pump, as e.g. been described in SE1251496-4 by the same applicant. Such pump, which in general is a piston pump used for hygienic applications such as homogenizers, utilizes a chamber formed between two membranes forming a seal between a liquid product, i.e. a hygienic side, and a hydraulic pressure source, i.e. a non-hygienic side. In order to detect a leakage a conductivity sensor is arranged in contact with the fluid between the two membranes. Hence, should a membrane be damaged whereby hydraulic oil is allowed to enter the hygienic side the conductivity will change, whereby an alarm may be triggered for initiating service or replacement of the membranes.

In the above application the pump is operated to increase the pressure from approximately 3 bar up to 250 bar during the course of each pump/suction stroke. The pressure in the pump chamber thus increases from a low pressure, such as 3 bar, to a high pressure, such as 250 bar in a periodical manner during operation. Even higher pressure may also be provided. Further to this elevated temperatures up to 140° C. may be provided, especially if the pump is arranged adjacent to heat treatment equipment.

It is required that the conductivity sensor is constructed to withstand the harsh environment in view of temperature and pressure inside the chamber. Further, the conductivity sensor should be operational for determining changes in the conductivity as such occur inside the pressure chamber.

In view of above, there is a need for an improved conductivity sensor for use in high pressure and high temperature applications. Further, there is a need for a high pressure pump for use in hygienic application having means for leakage detection.

SUMMARY

Accordingly, the present invention preferably seeks to mitigate, alleviate or eliminate one or more of the above-identified deficiencies in the art and disadvantages singly or in any combination and solves at least the above mentioned problems by providing a conductivity sensor, as well as a high pressure pump, in accordance with the appended claims.

According to a first aspect a conductivity sensor is provided. The sensor comprises at least one electrode being embedded in a cylindrical non-conductive body such that one end of each one of the at least one electrode is exposed to a sample volume, wherein the sensor further comprises a support body to which the cylindrical body is engagable with, which support body comprises means for attaching said support body to a frame structure in a fluid tight manner.

The non-conductive body may be formed by a sintering process, and the at least one electrode may be made of platinum.

The support body may be formed as a cylindrical body in which the non-conductive body is insertable.

In an embodiment, the sample volume may be formed as a recess in said non-conductive body.

According to a second aspect, a membrane assembly for a high-pressure pump is provided. The membrane assembly comprises a frame structure being sealed on opposite sides by two separate membranes, wherein said frame structure comprises a radial through hole for accommodating the non-conductive body as well as the support body of a conductivity sensor according to the first aspect.

The frame structure may have a circular shape.

According to a third aspect, a high pressure pump is provided. The pump comprises a membrane assembly according to the second aspect for transmitting pressure from a hydraulic side to a product side.

The high pressure pump may further comprise a control unit being connected to said conductivity sensor for determining any leakage from the hydraulic side and/or the product side into the membrane assembly.

According to a fourth aspect, a homogenizer is provided. The homogenizer comprises a high pressure pump according to the third aspect.

BRIEF DESCRIPTION OF DRAWINGS

These and other aspects, features and advantages of which the invention is capable of will be apparent and elucidated from the following description of embodiments of the present invention, reference being made to the accompanying drawings, in which FIG. 1 schematically illustrates a so-called wet-end of a homogenizer according to an embodiment, FIG. 2 schematically illustrates a wet end in a membrane equipped homogenizer according to an embodiment.

DETAILED DESCRIPTION

Figure 1:
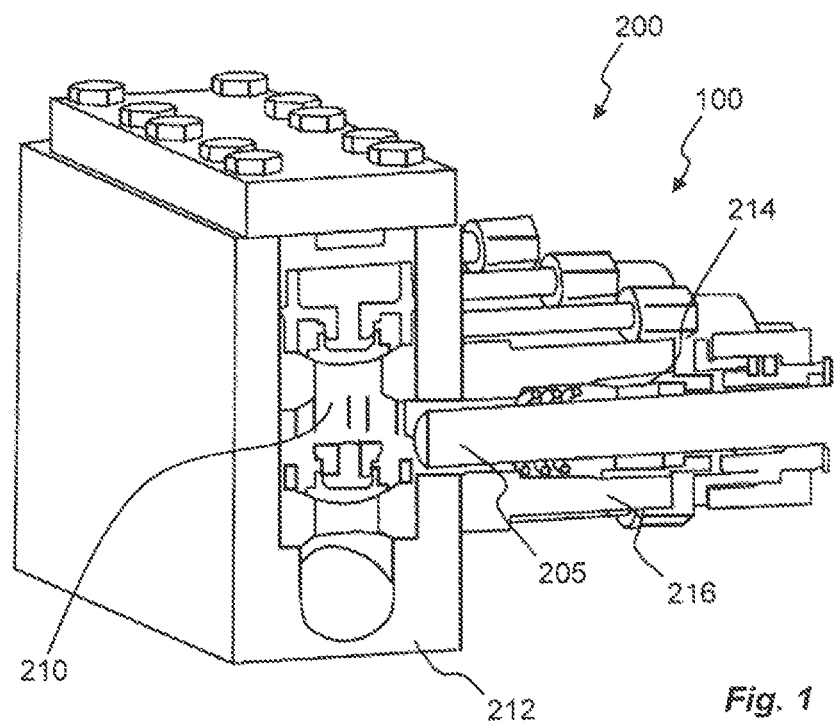

Starting with FIG. 1, a part of a homogenizer 100 is shown. According to a general principle the homogenizer 100 has two parts, namely a high pressure pump and a homogenizing device. The high pressure pump forms a high pressure and the homogenizing device provides one or several gaps through which the product is forced with the effect that smaller fat globules are formed, hence extending the life time of the product. The different components of an emulsion or a suspension have different physical properties, such as particle size etc. Given time, the difference in particle size leads to the product being divided into different component layers, e.g. creaming in milk. By decreasing the particle size, the rising velocity will be reduced thus extending the shelf life of the product. Further effects of homogenization is more appetizing colour, reduced sensitivity to fat oxidation, more full-bodied flavour and better stability of cultured milk products.

FIG. 1 is showing a so-called wet end 200 of a homogenizer 100. A piston 205 is provided and configured to move back and forth such that a high pressure is formed in a product chamber 210 of a pump block 212. One or several seals 214 are provided for keeping a tight fitting between the piston 205 and a piston receiving element 216. The one or several seals 214 also keep the product in the product chamber 210 apart from a crankcase and other non-hygienic parts of the homogenizer. In order to further make sure that unwanted micro-organisms do not end up in the product it is a common approach today to use steam barriers or the like in combination with the piston seals 214.

Figure 2:
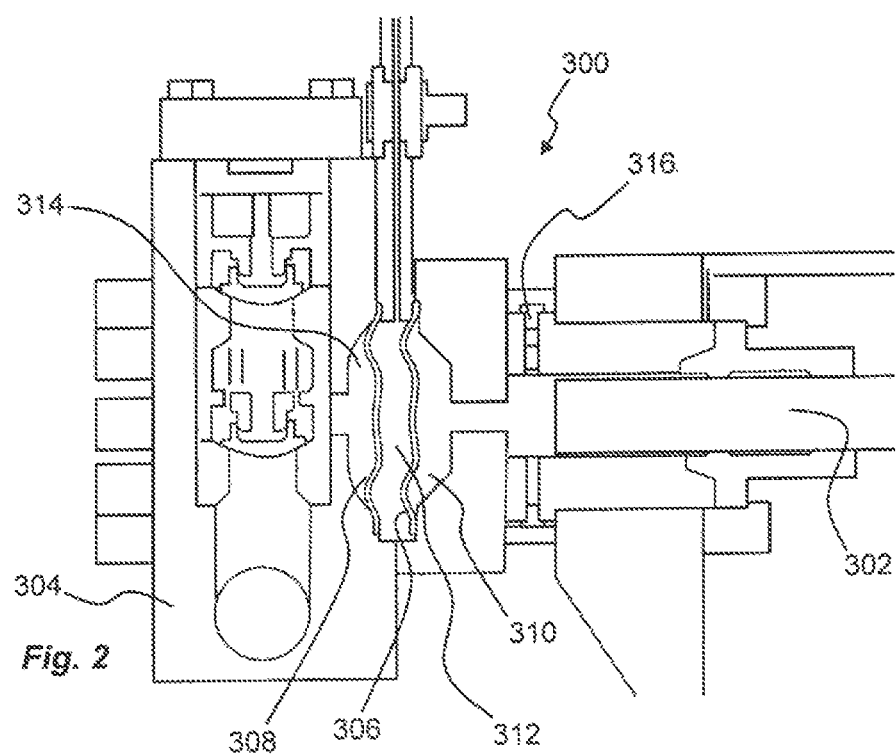

In FIG. 2 a wet end 300 of a membrane equipped homogenizer is shown. As the homogenizer illustrated in FIG. 1 a piston 302 is provided, or more correctly a pluriaty of pistons although only one of them is shown in FIG. 2. Further, the piston 302 is forming a high pressure in a pump block 304.

Unlike the homogenizer illustrated in FIG. 1 the wet end 300 is provided with a first membrane 306 and a second membrane 308. The first membrane 306 may be arranged such that a hydraulic oil chamber 310 and a membrane interior space 312, that is, a space formed between the first membrane 306 and the second membrane 308, are kept apart. The second membrane 308 may be arranged such that the membrane interior space 312 and a product chamber 314 are kept apart.

Further, a high pressure relief valve 316 may be connected to the hydraulic oil chamber 310 such that a pressure in the hydraulic oil chamber can be lowered by opening this valve. Although not illustrated, when opening the high pressure relief valve 316 hydraulic oil may be fed into a tank. This tank may also be connected to an inlet in the hydraulic oil chamber. A positive effect of this setup is that the hydraulic oil released via the high pressure relief valve 316 can be re-used.

The reason for having hydraulic oil is that this is used for forwarding the pressure formed by the piston 302 via the first membrane 306 and the second membrane 308 to the product chamber 314, but also for lubricating the seals and in that way extend the life time of the seals. Hence, unlike the wet end illustrated in FIG. 1 the piston 302 is indirectly forming a pressure in the product chamber 314.

An advantage of having membranes separating the product chamber 314 from the piston 302, crankshaft, crankcase and other parts placed on the non-hygienic side is that a well defined border is formed. An effect of this is that the risk that unwanted micro-organisms pass the membranes into is the product chamber 314 is significantly lowered. Even if the same degree of food safety may be achieved using for instance steam barriers, the membranes provide the benefit that no steam barriers are needed. The effect of this in turn is that the operational costs for running the homogenizer can be significantly reduced. Also from an environmental perspective, using less steam is of significant value.

A risk with membrane equipped homogenizers is that the membranes break and that hydraulic oil enters the product chamber. This may be a food safety hazard depending on the hydraulic oil being used, but it will with a high likelihood result in product losses. In order to overcome this risk, in the membrane interior space 312, that is, the space formed between the first membrane 306 and the second membrane 308, a conductivity sensor 400 is arranged.

The membrane interior space 312 is for this purpose enclosing a liquid or gel which is capable of transmitting a pressure and changing its conductivity when mixed with a hydraulic fluid or a product. Such liquid or gel may e.g. be brine gel.

Figure 3:
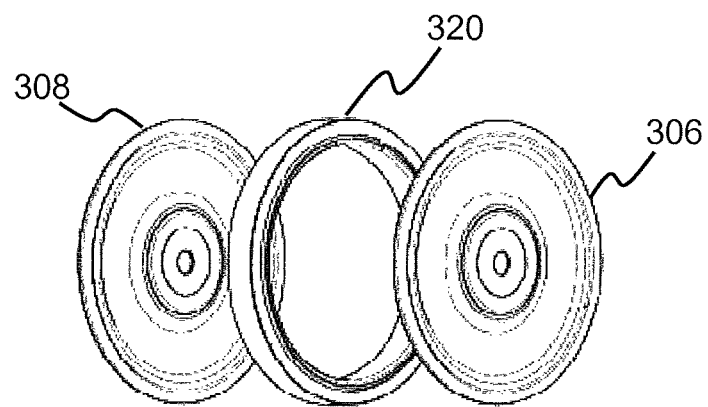
FIG. 3 is an exploded view of a membrane assembly according to an embodiment.

Now turning to FIG. 3 the membrane assembly is shown. The first membrane 306 is secured to a first side of a frame structure 320, while the second membrane 308 is secured to an opposite side of the frame structure 320. The frame structure 320 has a circular shape and a constant width such that the frame structure forms a cylindrical body. The membrane assembly is tightly sealed by appropriate gaskets or similar for preventing any leakage in the interface formed between the frame structure 320 and the membranes 306, 308.

Figure 4:
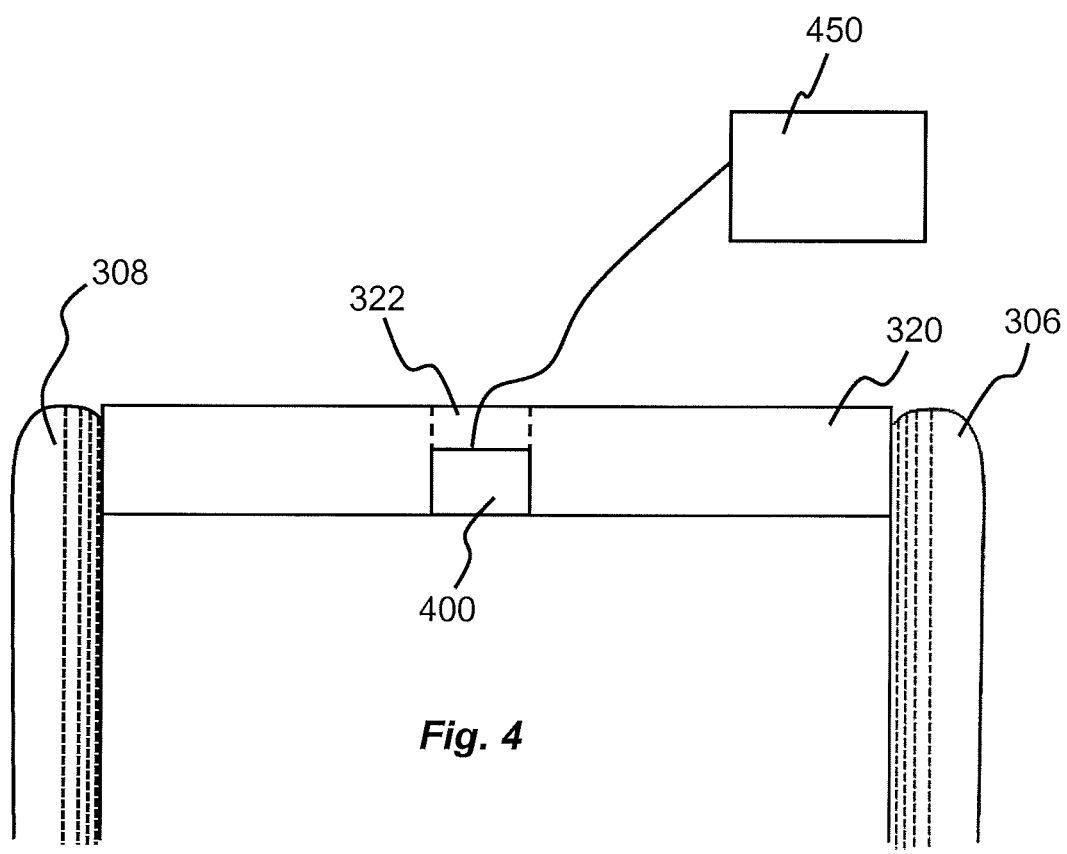
FIG. 4 is a semi-cross sectional view of the membrane assembly shown in FIG. 3.

The membrane assembly is further shown in FIG. 4. The frame structure 320 has a through hole 322 extending in a radial direction. A conductivity sensor 400 is inserted into the through hole in a fluid tight manner such that the liquid or gel enclosed within the membrane assembly will be in contact with the conductivity sensor 400. The sensor 400 is further connected to a control unit 450 configured to perform analysis of the data transmitted by the sensor 400 during operation.

Figure 5:
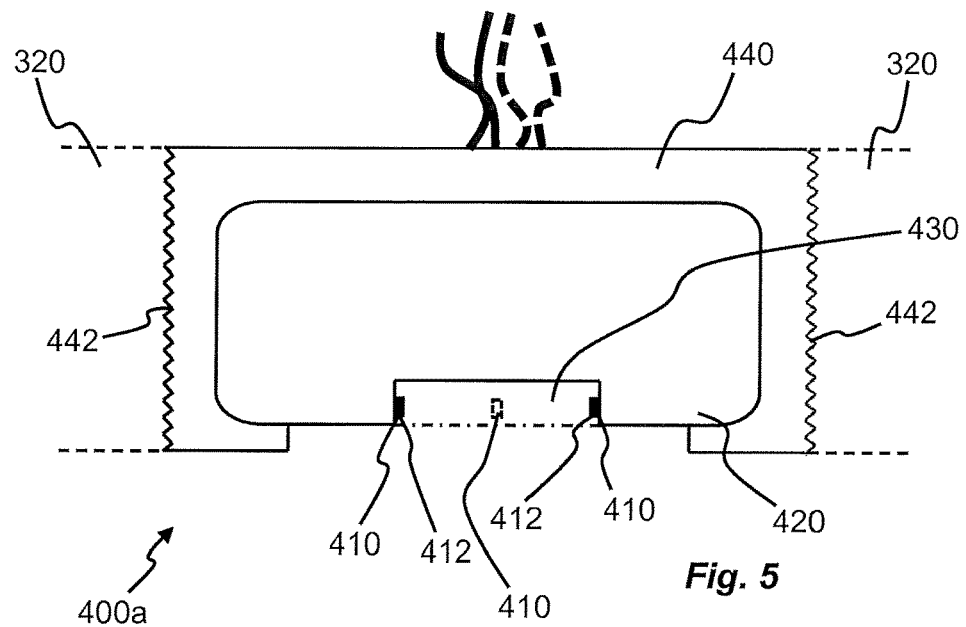
FIG. 5 is a side view of a conductivity sensor according to an embodiment.

An embodiment of a conductivity sensor 400a is shown in FIG. 5. The sensor 400a comprises a number of electrodes 410 being embedded in a cylindrical non-conductive body 420. One end 412 of each one of the electrodes 410 is exposed to a sample volume 430 being formed as a recess in the non-conductive body 420. A support body 440 is provided to which the cylindrical body 420 is engagable with, and the support body 440 comprises means for attaching the support body 440 to the frame structure 320 of the membrane assembly in a fluid tight manner.

As can be seen in FIG. 5 the support body 440 is formed as a cylindrical body being provided with outer threads 442 for engaging with corresponding threads on the inside of the through hole 322 of the frame structure 320. Further, the support body 440 comprises an interior volume for accommodating the non-conductive body 420. The non-conductive body 420 is held firmly in place inside the support body 440, e.g. by providing the support body 440 with flanges extending radially inwards and over the non-conductive body 420.

The sample volume 430 may in some embodiments be formed as a recess in the non-conductive body 420, such that the sample volume 430 is in fluid communication with the interior space of the membrane assembly. In other embodiment, the sample volume 430 may be formed by the interior space of the membrane assembly whereby the non-conductive body 420 may be made with a flat surface.

The upper end of the support body 420 may be provided with a conduit or channel for guiding electrical wires connecting to the electrodes 410. These wires may in turn be connected to the control unit 450, or to a wireless link which in turn is connected to the control unit 450.

Further, the upper end of the support body 420 is preferably provided with a recess for accommodating a tool used when attaching the sensor 400 to the frame structure 320.

Figure 6:
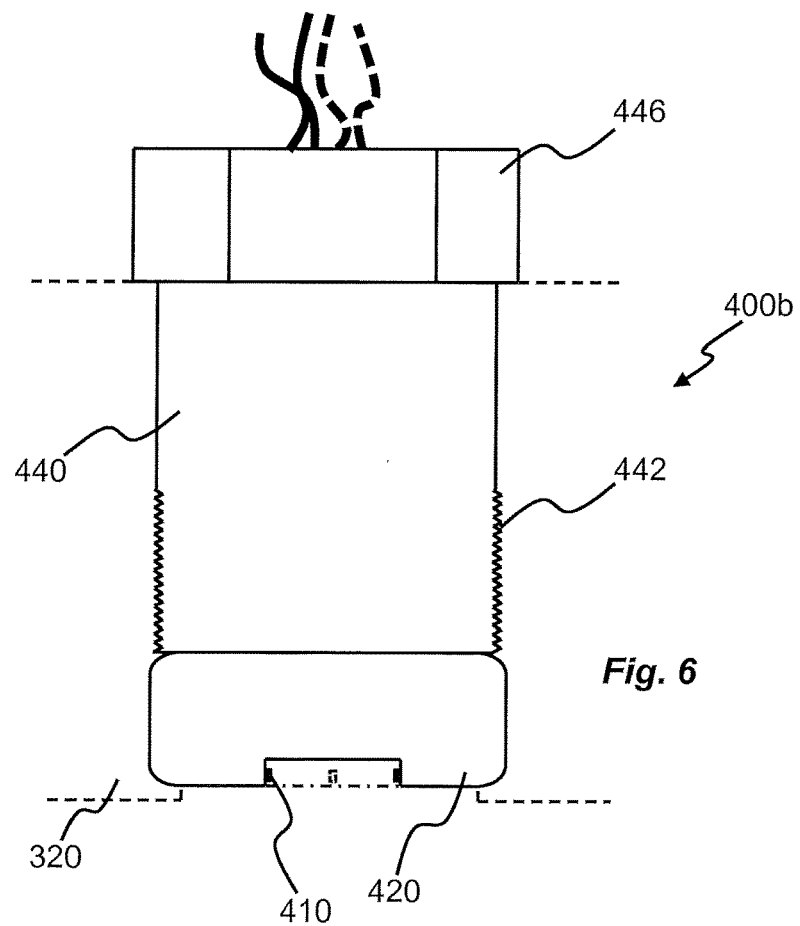
FIG. 6 is a side view of a conductivity sensor according to a further embodiment.

A further embodiment of a sensor 400*b* is shown in FIG. 6. The electrodes 410 and the non-conductive body 420 are similar to what has been described with respect to FIG. 5 and these will not be described in further detail here. However, the embodiment shown in FIG. 6 comprises a support body 440 which differs from the support body 440 of FIG. 5. In this embodiment there is no engagement between the non-conductive body 420 and the support body 440 except for a mechanical contact.

The support body 440 is formed as a bolt, wherein the end of the bolt presses against the non-conductive body 420. The threads of the bolt engages with inner threads of the through hole 322 of the frame structure 320. Further, the bolt 440 comprises an aperture for guiding the electrical wires needed for controlling the electrodes 410 of the sensor 400*b*. In addition to this, the bolt 440 is provided with an upper end 446 for engaging with a tool in order to screw the bolt downwards into the through hole 322. The upper end 446 may e.g. have a hexagonal shape.

The non-conductive body 420 is preferably made by a material which is capable of withstanding the harsh environment inside the membrane assembly, i.e. high pressure (up to 250 Bar) and high temperature (up to approximately 140° C.). In a preferred embodiment the non-conductive body 420 is formed by a sintering process, in which the electrodes 410 are arranged in the green body during the sintering process, after which additional milling of the non-conductive body 420 may be performed. In other embodiments the non-conductive body 420 may be made of metal, such as stainless steel, various ceramics, or thermoplastics.

The electrodes 410 also need to be made of a robust material, being capable of withstanding high pressure, high temperature, as well as the in some embodiments corrosive liquid or gel forming the conductive media within the membrane assembly. One suitable material for the electrodes 410 may be platinum; however other conductive materials may be suitable such as conductive ceramic materials, graphite, etc.

Figure 7A:
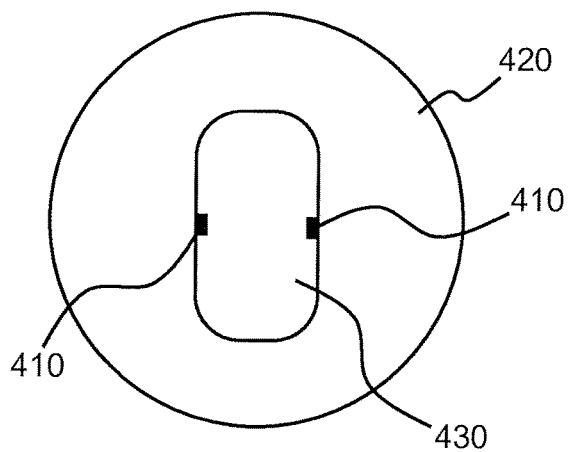
FIGS. 7a-d are end views of conductivity sensors according to different embodiments.
Figure 7B:
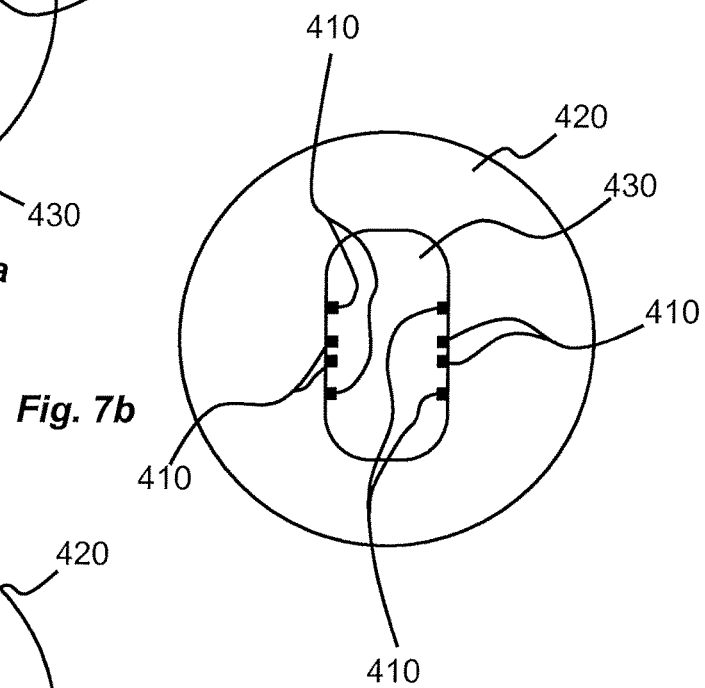
Figure 7C:
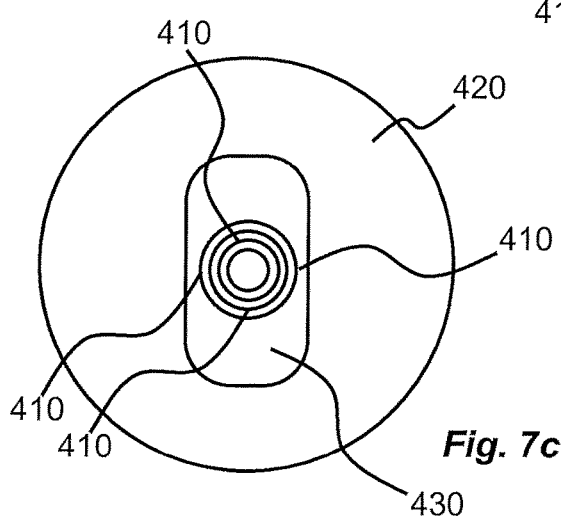

In FIGS. 7*a-c* different embodiments of the sensor 400 are shown. The non-conductive body 420 is shown having a recess 430 forming a sample volume. The electrodes 410 are arranged inside the recess 430 and exposed to any liquid or gel being present in the recess 430. In FIG. 7*a*, an embodiment is shown having two electrodes 410. The conductivity may e.g. be measured by applying a voltage over the two electrodes and measuring the current.

In FIG. 7*b* four electrodes are provided in pairs arranged on opposite sides of the sample volume. Each electrode 410 is circular, and each pair comprises two circular electrodes 410 arranged concentrically. During operation the outer electrodes 410 forms an AC cage around the inner electrodes 410, being provided with a DC current. Another embodiment is shown in FIG. 7*c* showing four circular electrodes arranged concentrically.

Figure 7D:
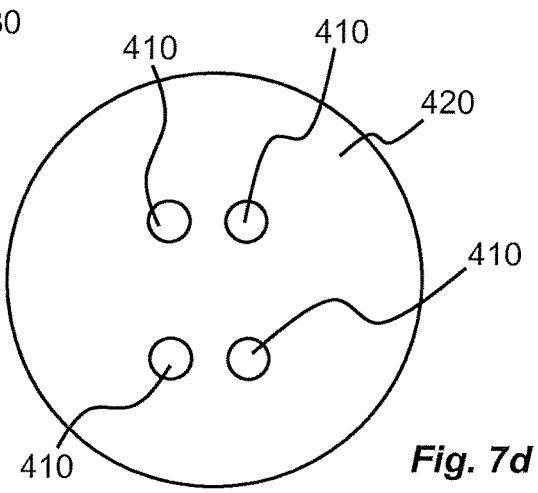

A yet further embodiment is shown in FIG. 7*d*. Four electrodes 410 are exposed at the surface of the sensor. There is a constant current between two current electrodes, whereby a voltage drop is measured across two voltage electrodes.

Although the present invention has been described above with reference to specific embodiments, it is not intended to be limited to the specific form set forth herein. Rather, the invention is limited only by the accompanying claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A homogenizer comprising:
a high pressure pump including a membrane assembly for transmitting pressure from a hydraulic side to a product side, the membrane assembly including a frame structure being sealed on opposite sides by two separate membranes, wherein the frame structure includes a radial through hole that is configured to receive a cylindrical non-conductive body; and
a conductivity sensor that is received in the radial through hole and has at least one electrode being embedded in the cylindrical non-conductive body such that one end of each one of the at least one electrode is exposed to a sample volume, and a support body to which the cylindrical non-conductive body is engagable with, which support body includes means for attaching said support body to the frame structure in a fluid tight manner,
wherein the sample volume is formed as a recess in the non-conductive body.

2. The homogenizer according to claim 1, wherein said non-conductive body is formed by a sintering process.

3. The homogenizer according to claim 1, wherein said at least one electrode is made of platinum.

4. The homogenizer according to claim 1, wherein said support body is formed by a cylindrical body in which the non-conductive body is insertable.

5. The homogenizer according to claim 1, wherein said sample volume is formed as a recess in said non-conductive body.

6. The homogenizer according to claim 1, wherein said frame structure has a circular shape.

7. The homogenizer according to claim 1, further comprising a control unit being connected to said conductivity sensor for determining any leakage from the hydraulic side and/or the product side into the membrane assembly.

8. A homogenizer comprising:
a pump block that includes a piston producing pressure in the pump block during operation of the homogenizer and communicating with a hydraulic oil chamber that is configured to contain hydraulic oil;
first and second spaced apart membranes in the pump block, the first and second membranes being spaced apart so that a membrane interior space exists between the first and second membranes, the membrane interior space being configured to contain a liquid or gel which transmits a pressure and changes conductivity when mixed with the hydraulic fluid or a product, the membrane interior space being separated from the hydraulic oil chamber by way of the first membrane;
a product chamber separated from the membrane interior space by the second membrane;
a frame structure positioned between and secured to both the first membrane and the second membrane;
a conductivity sensor positioned in a hole in the frame structure in a fluid-tight manner at a position so that when the liquid or gel is in the membrane interior space the conductivity sensor contacts the liquid or gel;

the conductivity sensor comprising a support body and a plurality of electrodes embedded in a cylindrical non-conductive body, one end of each of the electrodes being exposed to a sample volume in the cylindrical non-conductive body, the sample volume in the cylindrical non-conductive body communicating with the membrane interior space, the support body including an interior volume that accommodates the cylindrical non-conductive body, the support body and the hole in the frame structure possessing structure by which the support body engages and is held in hole in the frame structure.

9. The homogenizer according to claim 8, wherein the frame structure possesses a cylindrical shape.

10. The homogenizer according to claim 8, wherein the hole in the frame structure is a through hole.

11. The homogenizer according to claim 8, wherein the structure by which the support body engages and is held in hole in the frame structure includes outer threads on an outer surface of the support body and inner threads inside the hole, the outer threads engaging the inner threads to hold the support body in the hole in the frame structure.

12. The homogenizer according to claim 8, wherein the sample volume is a recess.

13. The homogenizer according to claim 8, wherein the plurality of electrodes includes more than two electrodes.

* * * * *